(12) United States Patent
Murray

(10) Patent No.: US 7,649,632 B2
(45) Date of Patent: Jan. 19, 2010

(54) CHARACTERIZATION OF MICRO- AND NANO SCALE MATERIALS BY ACOUSTIC WAVE GENERATION WITH A CW MODULATED LASER

(75) Inventor: Todd W. Murray, Brookline, MA (US)

(73) Assignee: The Trustees of Boston University, Boston, MA (US)

( * ) Notice: Subject to any disclaimer, the term of this patent is extended or adjusted under 35 U.S.C. 154(b) by 402 days.

(21) Appl. No.: 10/593,655

(22) PCT Filed: Mar. 23, 2005

(86) PCT No.: PCT/US2005/009726

§ 371 (c)(1),
(2), (4) Date: May 29, 2007

(87) PCT Pub. No.: WO2005/094503

PCT Pub. Date: Oct. 13, 2005

(65) Prior Publication Data

US 2007/0273952 A1    Nov. 29, 2007

Related U.S. Application Data

(60) Provisional application No. 60/555,427, filed on Mar. 23, 2004.

(51) Int. Cl.
*G01B 9/02*    (2006.01)
(52) U.S. Cl. .................................................. 356/502
(58) Field of Classification Search ....................... None
See application file for complete search history.

(56) References Cited

U.S. PATENT DOCUMENTS

| 4,046,477 A | 9/1977 | Kaule |
| 5,546,187 A | 8/1996 | Pepper et al. |
| 6,008,906 A | 12/1999 | Maris |

*Primary Examiner*—Hwa S Lee (Andrew)
(74) *Attorney, Agent, or Firm*—Weingarten, Schurgin, Gagnebin & Lebovici LLP

(57) ABSTRACT

Apparatus for analyzing thin surface layers. An acoustic wave generating laser beam is amplitude modulated with continuous wave modulation of a frequency in the megahertz to gigahertz range and an optical system directs the modulated radiation to a surface of a thin surface layer. This in turn causes an acoustic wave that is sensed and analyzed to provide an indication of properties of thin surface layer.

20 Claims, 14 Drawing Sheets

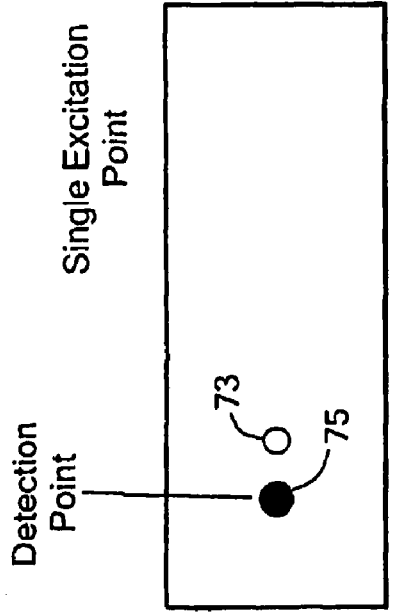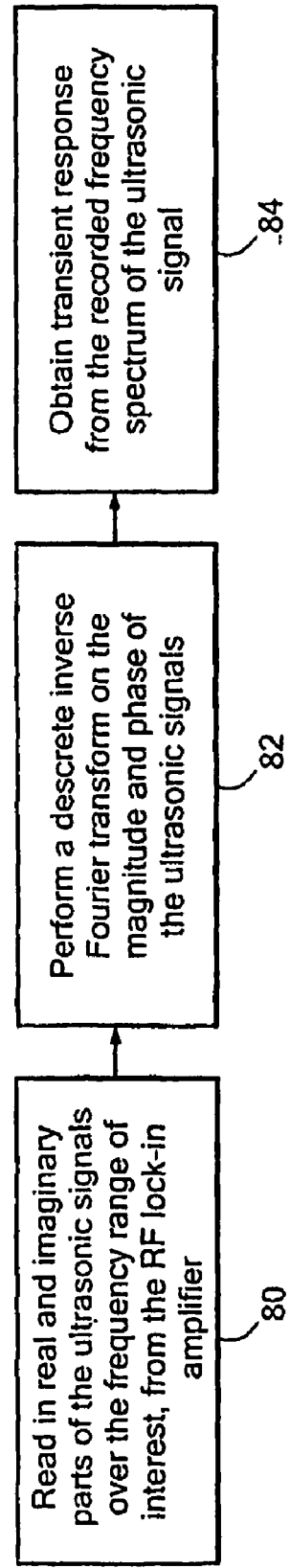
FIG. 4a
FIG. 4b

Acoustic response of an aluminum half-space showing SAWs generated using CW and pulsed laser sources. The laser sources produce the same maximum surface temperature.

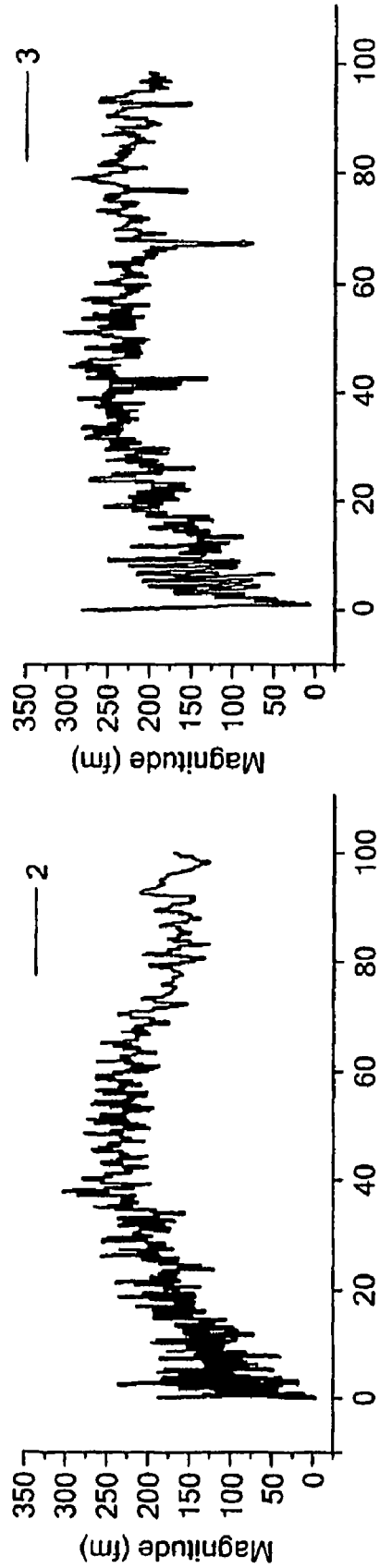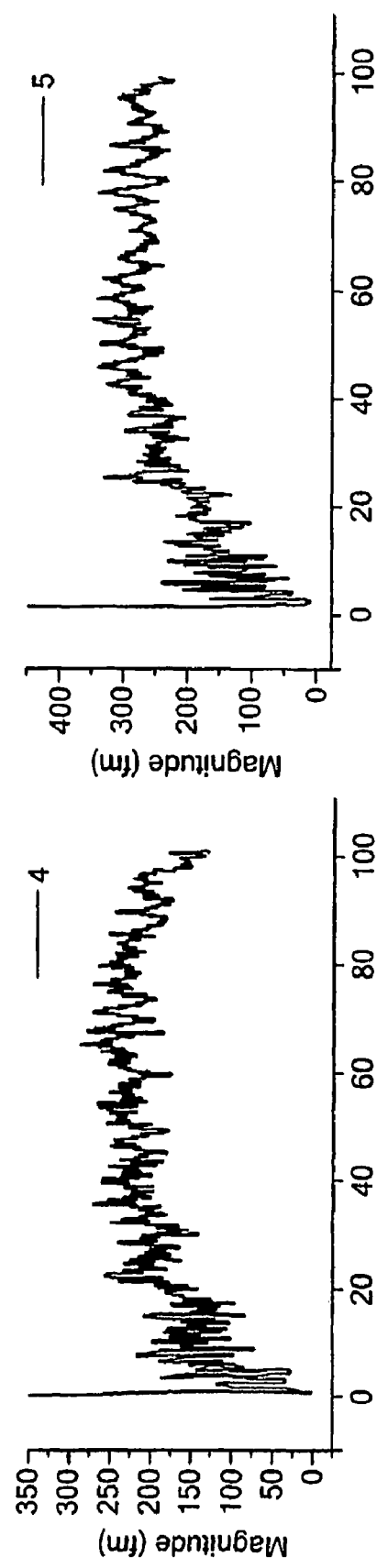
FIG. 6a  FIG. 6b  FIG. 6c  FIG. 6d

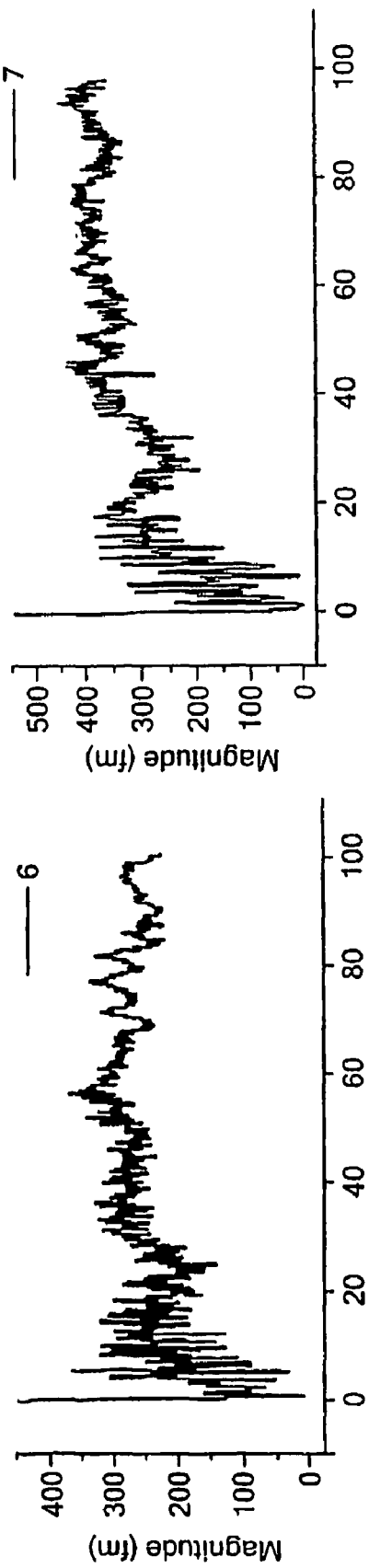
FIG. 6f
FIG. 6e
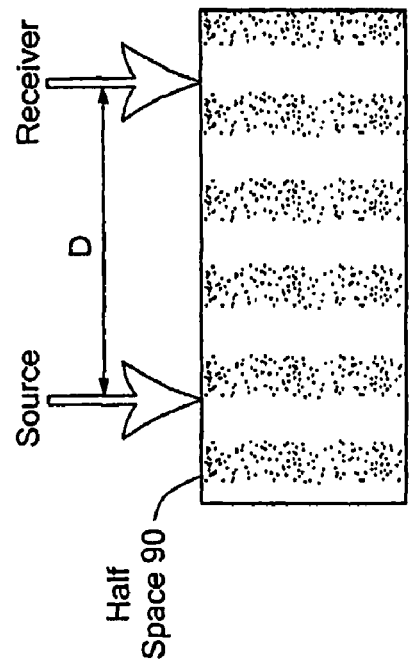
FIG. 6g

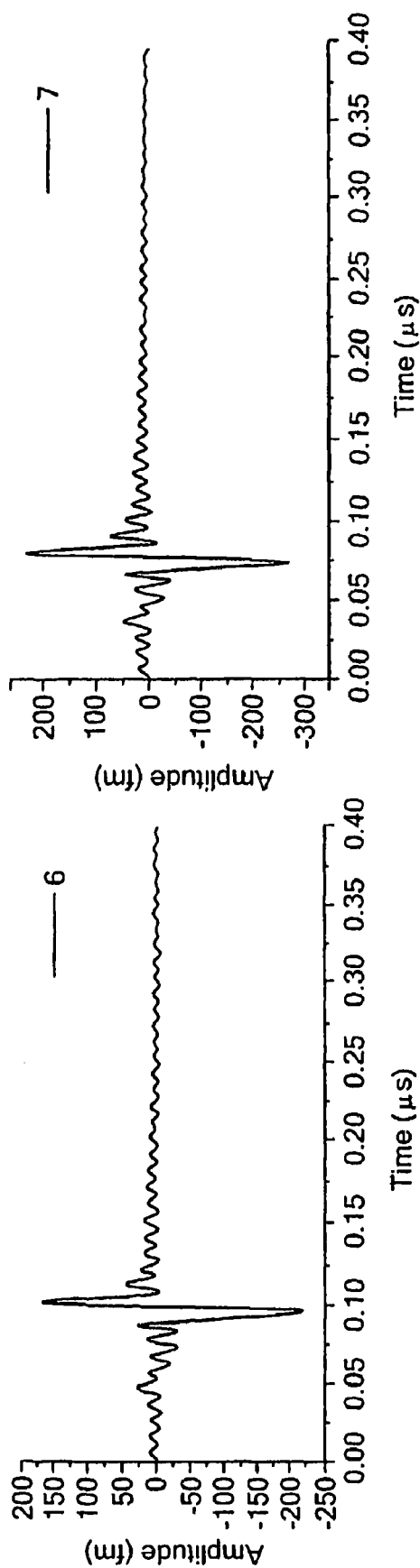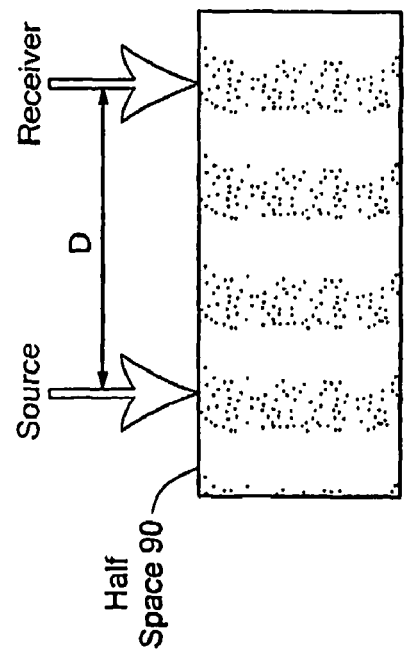
FIG. 7f
FIG. 7e
FIG. 7g

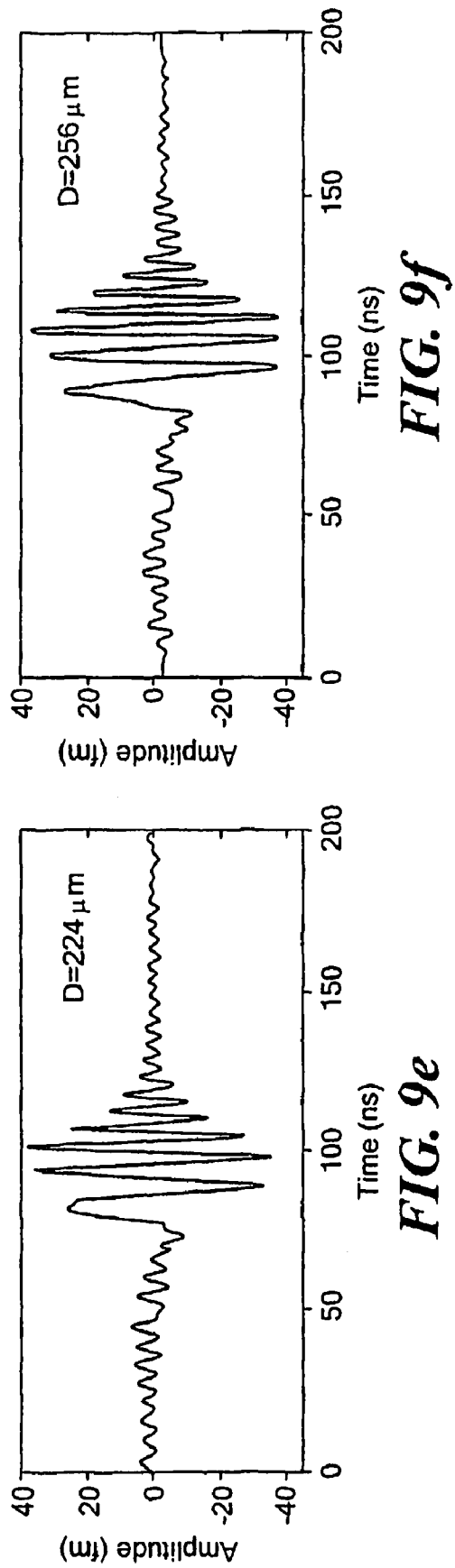
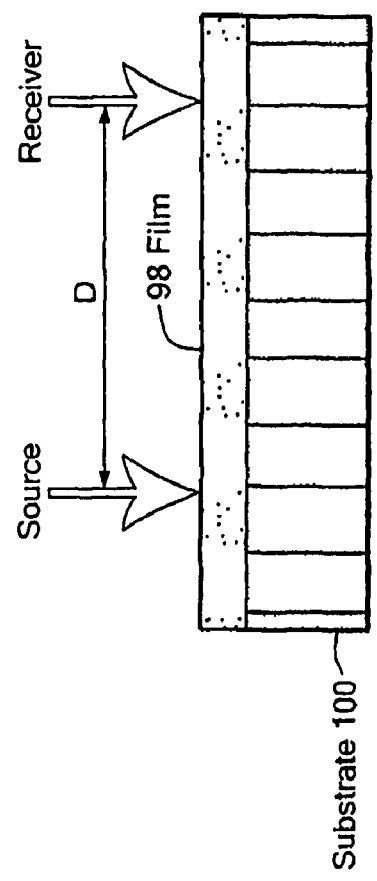
FIG. 9e
FIG. 9f
FIG. 9g

CHARACTERIZATION OF MICRO- AND NANO SCALE MATERIALS BY ACOUSTIC WAVE GENERATION WITH A CW MODULATED LASER

CROSS REFERENCE TO RELATED APPLICATIONS

This application claims the benefit under 35 U.S.C. § 119 (e) of U.S. Provisional Application No. 60/555,427 filed on Mar. 23, 2004 entitled Device and Method for High Sensitivity Laser Ultrasonic Characterization of Micro- and Nanoscale Materials, the disclosure of which is incorporated herein by reference.

STATEMENT REGARDING FEDERALLY SPONSORED RESEARCH OR DEVELOPMENT

Not applicable

BACKGROUND OF THE INVENTION

This invention relates to a laser based system to measure the physical and mechanical properties of thin films, plates, and coating materials. Currently existing laser ultrasonic techniques for the characterization of such materials use pulse laser sources for the generation of acoustic waves. Short laser pulses from femto second to nanosecond second lasers generate broad bandwidth acoustic waves, and detection of these waves is accompanied by the presence of broadband noise in the measurement system. This degrades the signal-to-noise ratio of the measurement limits the accuracy with which the relevant material properties can be determined.

BRIEF SUMMARY OF THE INVENTION

The present invention relates to a narrow bandwidth laser based system which uses a high frequency modulated continuous wave laser source to generate narrow bandwidth acoustic waves combined with a narrow-bandwidth detection scheme. According to the present invention, an acoustic microscopy technique is presented which uses a continuous wave (CW) amplitude modulated laser source for the generation of narrow band acoustic waves for use in analysis of thin materials and micro- and nanoscale plates, membranes, and coatings. An acoustic wave generating laser beam is amplitude modulated with continuous wave modulation of megahertz-gigahertz frequency range and an optical system directs the modulated radiation to a surface of a test specimen. This in turn causes an acoustic wave that is optically sensed using an interferometer and analyzed in the time domain and/or frequency domain to provide an indication of properties of the test specimen.

This invention allows for the displacement sensitivity to be improved over other laser based ultrasonic inspection techniques through a narrowing of the bandwidth of the detection system. The energy in the generated acoustic signal is centered at the frequency of modulation of the laser generation source. The effective bandwidth of the acoustic signal is inversely proportional to the length of time that the surface is illuminated. The bandwidth of the optical detection system may then be reduced to match that of the acoustic signal, thus allowing for a substantial improvement in the signal to noise ratio of the detection system. This narrow band measurement is made, for example, using a lock-in amplifier or vector network analyzer, and the bandwidth can be easily selected based on the signal to noise ratio requirements for a given application. This system is capable of modulating the amplitude of the laser source, and hence generating acoustic waves, over a broad range of frequencies from the low megahertz to tens of gigahertz.

This invention allows for the generation of high frequency acoustic waves with short wavelengths that are suitable for inspecting small scale systems such as thin films and coatings. It is well suited to measure the mechanical properties of thin films such as the elastic moduli and density, as well as the dimension properties such as thickness. It is also suitable for the inspection of other small-scale structures such as micro- or nanoscale beams, membranes, or plates. The invention also can be used to generate and detect acoustic waves in macroscopic systems for nondestructive evaluation and determination of physical and mechanical properties. These applications include the detection of subsurface or surface breaking cracks and the detection of subsurface voids or disbonds.

BRIEF DESCRIPTION OF THE SEVERAL VIEWS OF THE DRAWING

These and other features of the present invention are illustrated in the detailed description below in conjunction with the drawing of which:

FIGS. 4a and 4b illustrate frequency domain processing of the acoustic response according to the invention;

FIGS. 6a-6g illustrate the measured frequency response of a standard material.

FIGS. 7a-7g illustrate a time domain response of a standard material, reconstructed from the frequency domain data of FIGS. 6a-6g, for reference purposes;

FIGS. 9a-9g illustrate the use of the invention in analysis of a thin gold layer.

DETAILED DESCRIPTION OF THE INVENTION

The present invention presents a technology for acoustic microscopy using lasers amplitude modulated with continuous wave modulation at frequencies into the GHz frequency range. The signal to noise ratio of optical detection systems is inversely proportional to the bandwidth of the system. By sinusoidally modulating a CW laser beam applied to the surface of the target material, it is possible to produce very narrow-bandwidth acoustic waves and hence narrow the bandwidth of the optical detection system to match that of the acoustic waves. The signal-to-noise ratio of such a CW modulated laser system represents an improvement of several orders of magnitude over that of previous laser ultrasonic systems which use pulsed laser sources to generate high frequency, broad bandwidth acoustic waves.

Figure 1:
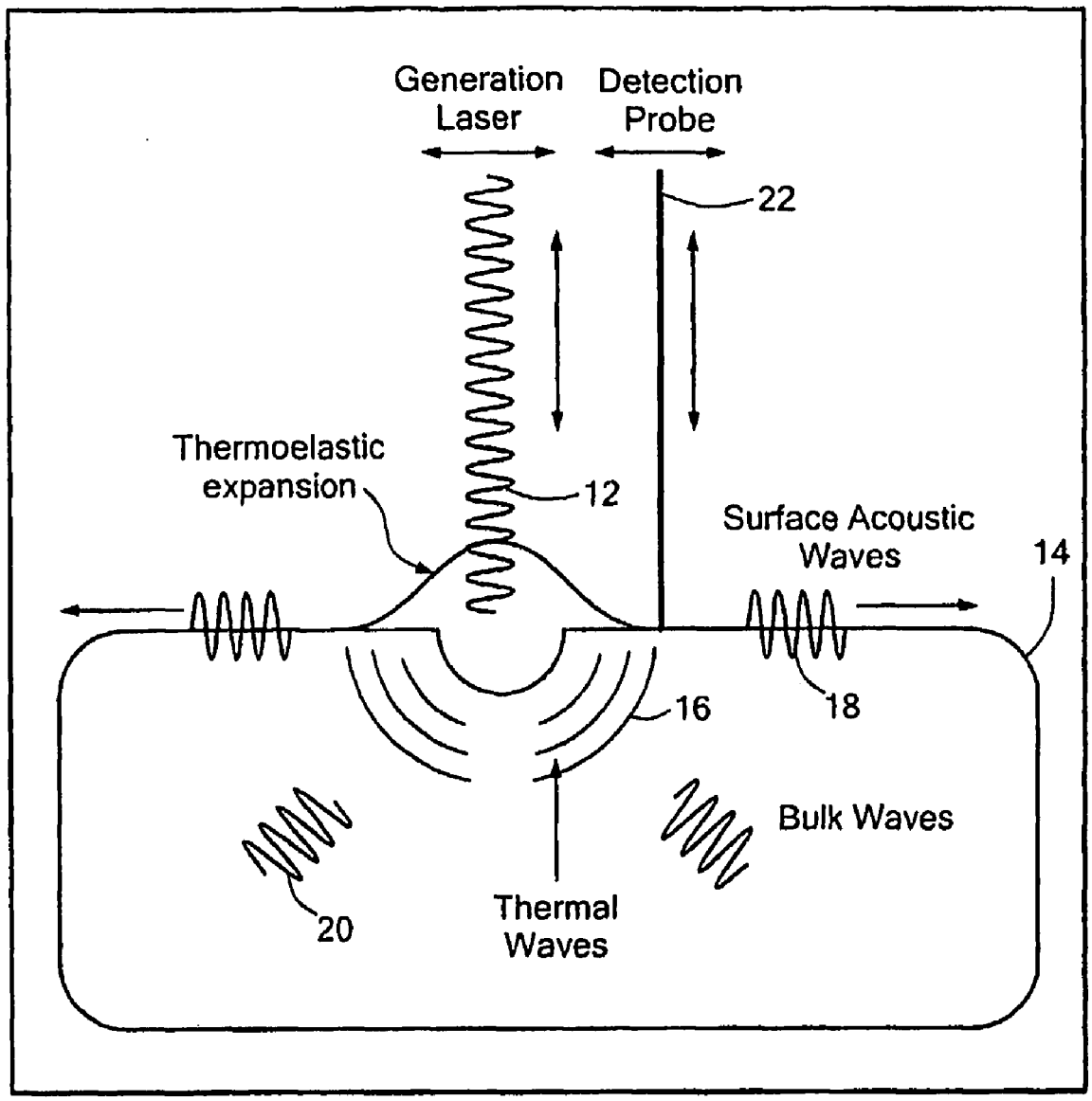
FIG. 1 illustrates the creation and sensing of an acoustic wave from a CW modulated laser in a material using laser beams.

The CW amplitude modulated laser beam such as laser beam 12 in FIG. 1 is applied to a thin material or a surface layer of a thin or other material 14 where it creates both thermal waves 16, surface acoustic waves (SAW) 18 and bulk waves 20. The applied beam 12 is for example, in the wavelength range of 1500 nanometers (nm) and may be modulated at up to 40 gigahertz using, for example, an electroabsorption or Mach Zehnder modulator. Sources at 1,300 and 1,064 nm, for example, may also been used. The material 14 responds to heating to create acoustic waves on 18 which can be detected by a detection beam 22, typically from a second laser source, described below. The surface perturbations caused by the SAW wave 18 are interferometrically detected and the detection signal used to analyze properties of the material 14 as described herein below.

Figure 2:
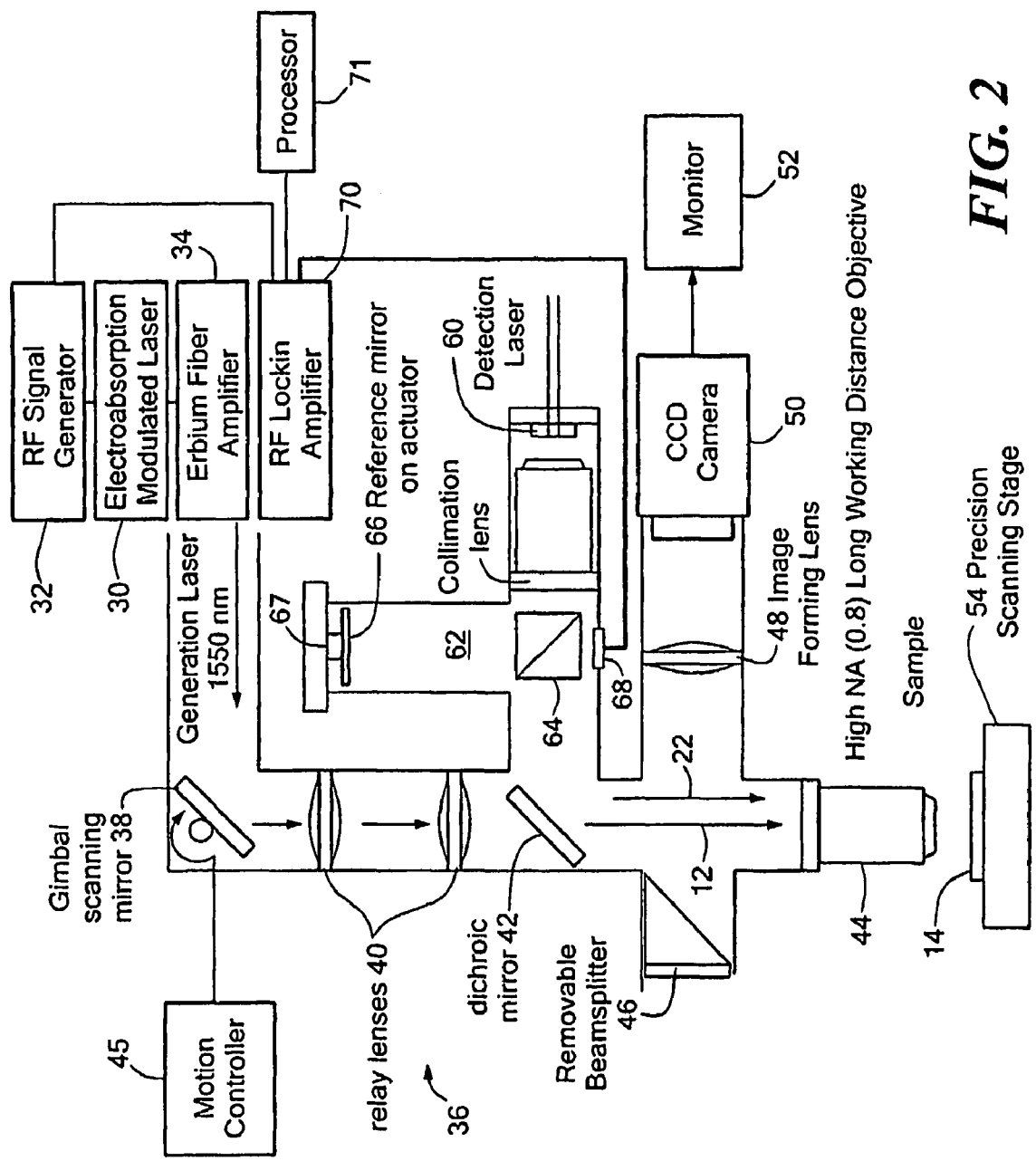
FIG. 2 illustrates a system for the purpose of FIG. 1.

FIG. 2 illustrates the apparatus for performing the acoustic testing of a sample material 14. A laser 30 which may be a DBF diode laser is CW amplitude modulated using an electro-absorption, Mach-Zehnder, or electro-optic modulator. The signal to the modulator is provided by a RF signal generator 32 at a modulation frequency in the megahertz-gigahertz range, this range can be from less than 1 MHz –40 GHz, or more. The laser 30 provides an output radiation typically in the near infrared wavelengths, for example 1550 nm. The output of laser 30 is amplified by an amplifier 34, typically an erbium fiber amplifier that also controls the power in the beam applied to the material. The output of the amplifier is applied to an optical path 36 consisting of a scanning mirror 38, relay lenses 40, dichroic mirror 42 and focusing objective lens 44 which focuses the radiation, typically to spot size of 100's of nanometers to a few microns on the sample 14. The gimbal scanning mirror 38 allows for the excitation laser source to be scanned within the field of view of the microscope objective under control of a controller 45.

A viewing system consisting of a prism 46 can slide into the optical path 36 and direct a portion of the radiation reflected from sample 14 through an imaging lens 48 to a video camera 50. A monitor 52 detects the signal from the video camera 50 and allows the operator to view the sample surface for sample alignment via stage 54. A second or detection laser 60 is placed in an interferometer such as a Michelson interferometer 62. Its output is typically in the visible radiation range. Laser 60 applies its radiation through a beam splitter 64 to the mirror 42 to provide the detection beam 22 in FIG. 1. The detection beam is phase modulated by the acoustic wave produced by the modulated excitation source on the sample surface.

The interferometer is formed by an orthogonally placed reference mirror 66 on an actuator 67. The actuator on the reference mirror used to control the path length of the reference beam. The reference and detection beam return to the beamsplitter 64 and interfere allowing for the phase modulation on the reference beam to be converted to an intensity modulation, which is subsequently detected by the photodetector 68. The signal from the photo detector 68 is applied, along with the signal from the RF signal generator 32 to a lock-in amplifier or vector network analyzer 70. The magnitude and phase of the acoustic signal are detected using the lock-in amplifier or vector network analyzer. This signal is fed to a processor 71 which performs signal manipulations and processing algorithms described below.

The measurement system described thus far allows for the measurement of the real and imaginary components of the acoustic wave field, or, equivalently, the magnitude and phase of the acoustic waves generated by the modulated source. This data must then be processed to obtain acoustic wave velocity information or to detect material defects. In the inspection of thin films, for example, SAW velocity is important. SAWs that propagate on a film/substrate system are dispersive. The penetration depth of SAWs depends on their wavelength. High frequency (short wavelength) SAWs interact primarily with the near surface region while low frequency (long wavelength) SAWs penetrate further into the material. The SAW velocity depends on the elastic moduli, Poisson's ratios, densities, and thicknesses of each of the coating layers and the substrate. Using theoretical models for SAW propagation in layered media, the properties of thin films are found if the dispersion curves can be determined experimentally.

Figure 3A:
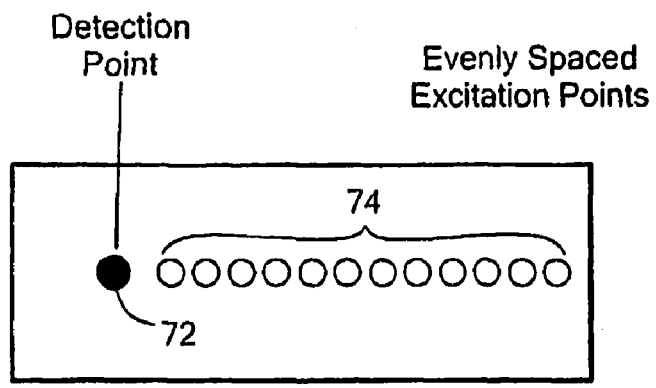
FIGS. 3a and 3b illustrate the steps of time domain processing of the acoustic response according to the invention.
Figure 3B:
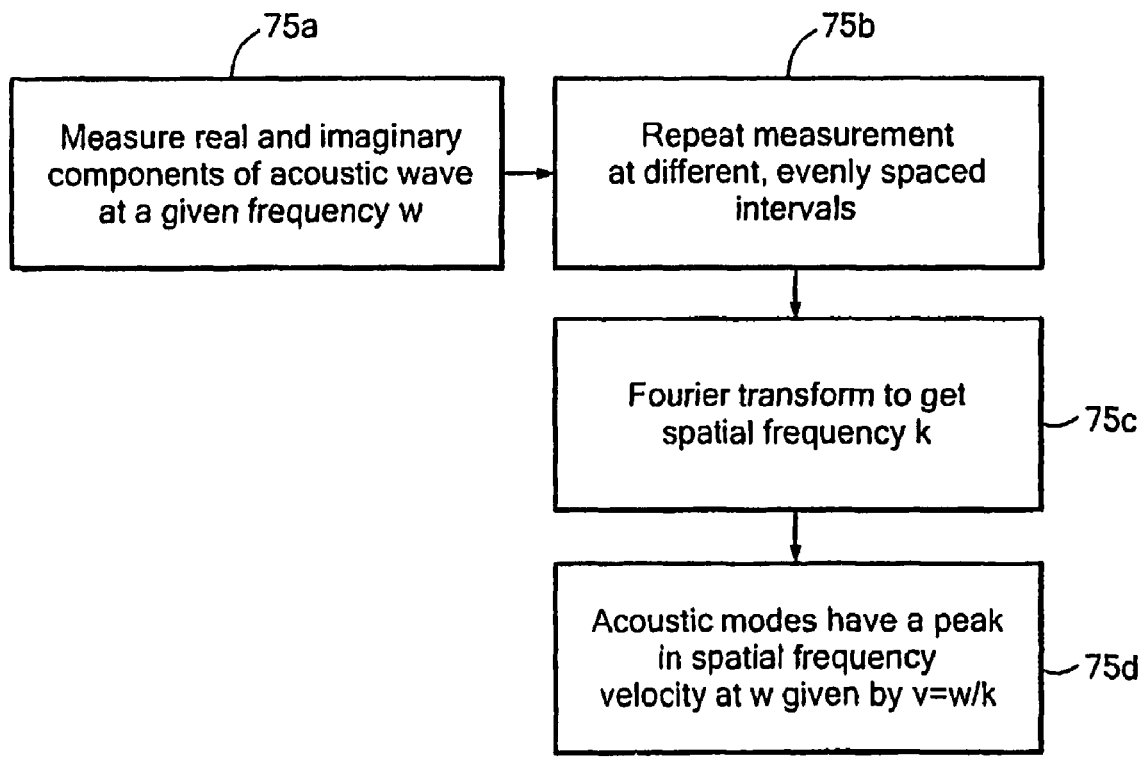

With reference to FIG. 3 there is shown a schematic of the experimental configuration showing one detection point 72 and several excitation points 74 evenly spaced on the surface of the specimen that result from activation of mirror 38. The detector may be held fixed and the source scanned with the real and imaginary parts of the acoustic wave field measured at each excitation point. In another embodiment, the source may be held fixed and the detection point scanned in equally spaced increments. At a given excitation frequency the real and imaginary components of the acoustic wave field are obtained as a function of space using processor 71 and the flow chart of step 75a-75d in FIG. 3. This date is Fourier transformed and the magnitude taken giving the magnitude at each spatial frequency. Peaks in spatial frequency correspond to acoustic modes in the system. The temporal excitation frequency w is divided (step 75a) by the peak spatial frequency k, giving the velocity v at w through v=w/k. This process can be repeated at several temporal frequencies to obtain the dispersion curve for the system as shown below.

With reference to FIG. 4 there is shown an alternate processing flow diagram. In this case the source and receiver point are held fixed at points 73 and 75 and the temporal frequency is scanned over the frequency range of interest in step 80. The result is that the real and imaginary components of the acoustic wave field are measured over the entire frequency range. An inverse Fourier transform of the data is then taken at step 82 resulting in a synthesized time domain response of the system. This is the response of the system to a "pulse like" excitation source given by the inverse Fourier transform of the (real and imaginary components) excitation laser source in step 84. This synthesized time domain trace may be processed through standard techniques to obtain velocity dispersion curves, or it may be used, for example, to detect transient acoustic responses associated with material defects or inhomogeneities.

Figure 5:
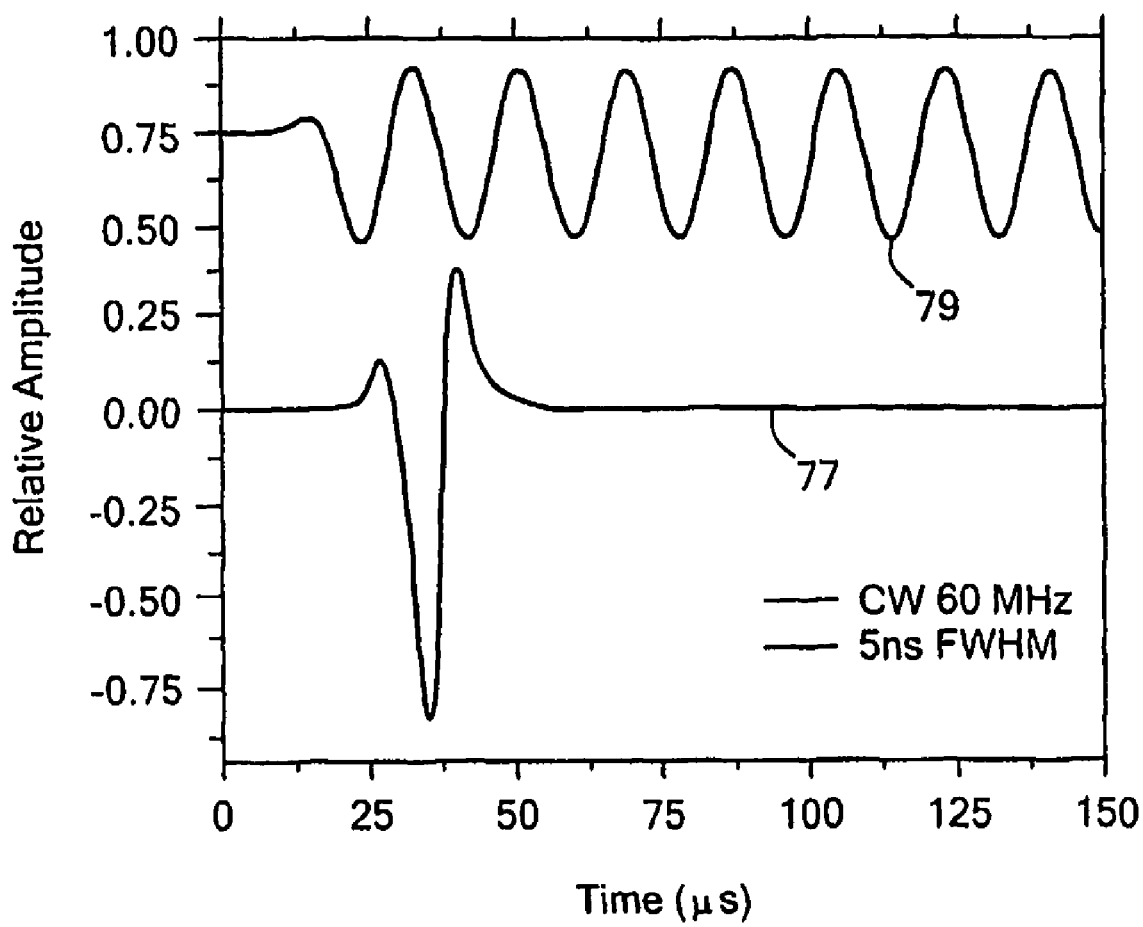
FIG. 5 illustrates the response of a material to pulse versus CW modulated laser radiation.
Figure 7A:
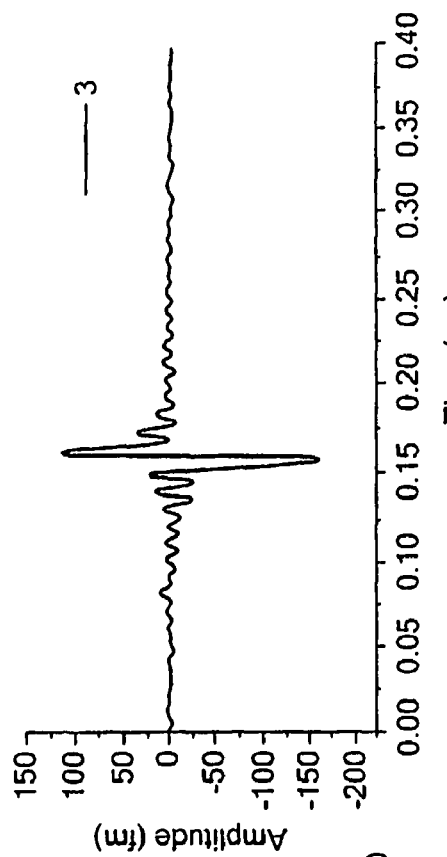
Figure 7B:
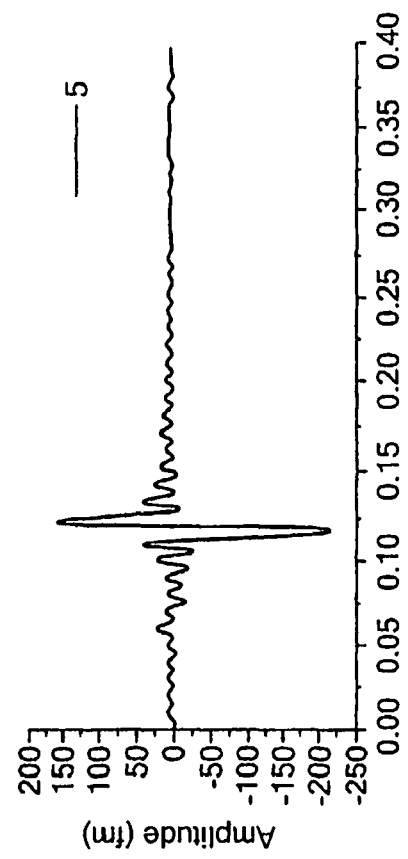
Figure 7C:
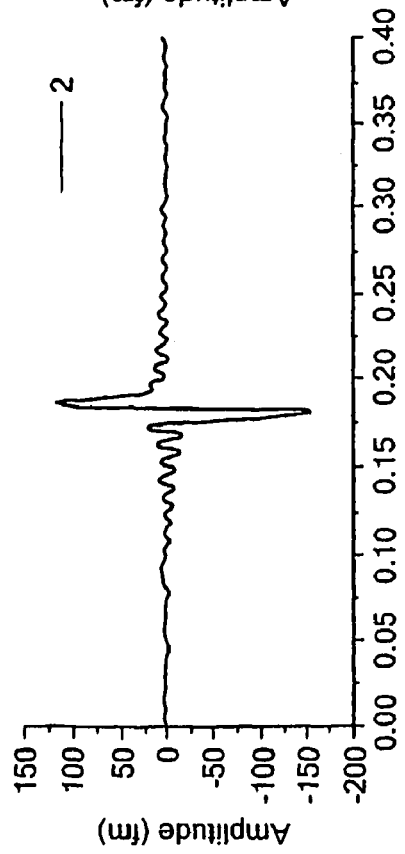
Figure 7D:
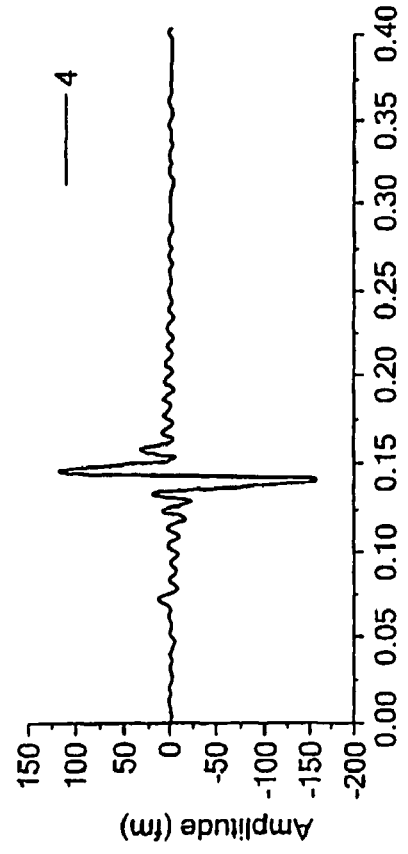

Referring now to FIG. 5, theoretical results are shown for surface acoustic waves generated using pulsed and CW modulated laser sources. These were calculated by numerically solving the equations of thermoelasticity, and show the displacement of the sample surface after illuminating it with the given source. The amount of laser power that is used in the calculation is fixed such that the two laser sources produce the same surface temperature rise. For thermoelastic generation of acoustic waves, there exists some temperature $T_{max}$ (typically taken as the melting point) that the sample surface is kept below in order to avoid damage or ablation. For a given laser pulse shape, this limits the maximum allowable absorbed power density at the surface. As an example, laser heating with a 5 ns Gaussian laser pulse is compared with that produced by a 60 MHz CW laser source. The laser spot size is taken as 3 microns. It is found that, for the same absorbed power density in each case, the CW laser heats the material to a temperature of approximately 2.5 times higher than the pulsed laser. This is due to the fact that heat builds up in the sample between cycles until the sample reaches steady state. With the CW laser power scaled down by a factor of 2.5 both of the laser sources produce equivalent surface heating. The scaled pulse shapes are then convolved in processor 71 with the impulse response of an aluminum semi-infinite half space (with the source and receiver slightly offset on the sample surface) to find the acoustic response of the sample. The resulting signals are shown in FIG. 5. As is evident in the pulsed laser case, the laser source produces a strong surface acoustic wave (SAW) 77. The CW response is shown at 79. For laser powers that produce equivalent surface heating, the SAW displacement amplitude produced by pulsed generation is a factor of about 2.5 higher than that of CW generation, but the bandwidth of the CW signal can be substantially reduced through detection with an RF lock-in amplifier or vector network analyzer. Using a sufficiently long integration time, the bandwidth can be reduced by six orders of magnitude for the narrowband case over the broadband case resulting in a SNR increase of three orders of magnitude for this particular example. SNR is an important issue in laser based systems, which have substantially lower sensitivity than conventional contact transducers, and this type of SNR increase could open up the possibility of using these non-contact systems for a much wider range of inspection applications.

Referring now to FIGS. 6a-6g and 7a-7f there is illustrated processing to establish a base line for the acoustic response of the system using a half space aluminum plate 90 for a reference standard. This provides a calibration standard for use in analysis of other acoustic responses to other thin surface layers or thin materials. FIGS. 6a-6f illustrate the magnitude of the acoustic wave field measured in the experiment as a function of frequency. This is found by taking the square root of the sum of the squared real and imaginary components of the signal. It is observed that displacements in the femtometer range can be measured. The processing technique of FIG. 4 has been used to obtain the time domain response of the system. The reconstructed signals at six different points in the application of a CW modulated laser beam to the aluminum half space 90 are given in FIGS. 7a-7f. The signals are in agreement with those that would be expected from a pulsed laser source. However, they are instead obtained from a CW modulated source which is scanned in frequency over the bandwidth of interest with each measurement being made at an extremely narrow bandwidth. The bandwidth for these measurements was 0.7 Hz and may be easily controlled through the integration time of the lock-in amplifier 34. The displacement sensitivity surpasses that which is possible with comparable surface heating using a pulsed source.

Figure 8A:
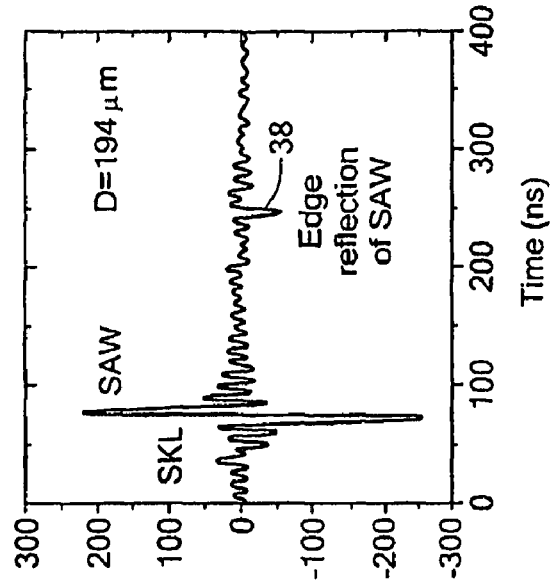
FIGS. 8a-8c illustrate use of the invention in detection of a fault in a material using time domain processing.
Figure 8B:
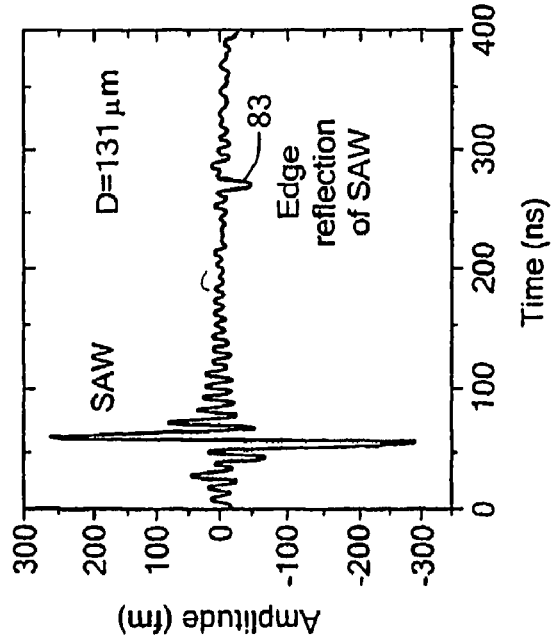
Figure 8C:
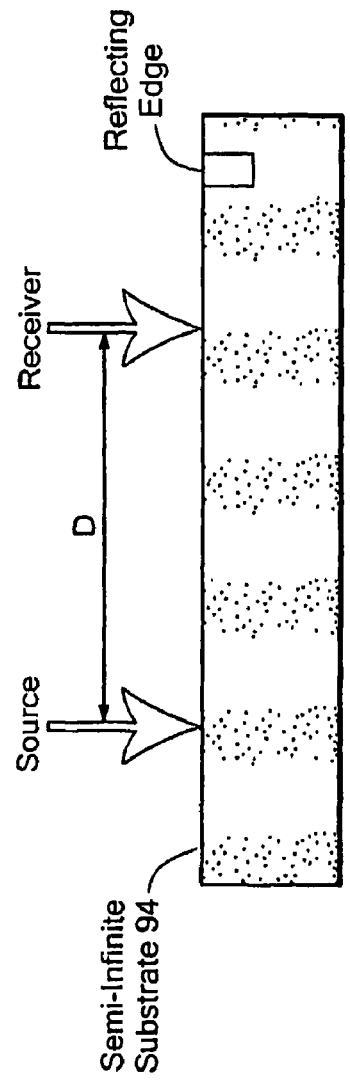
Figure 9A:
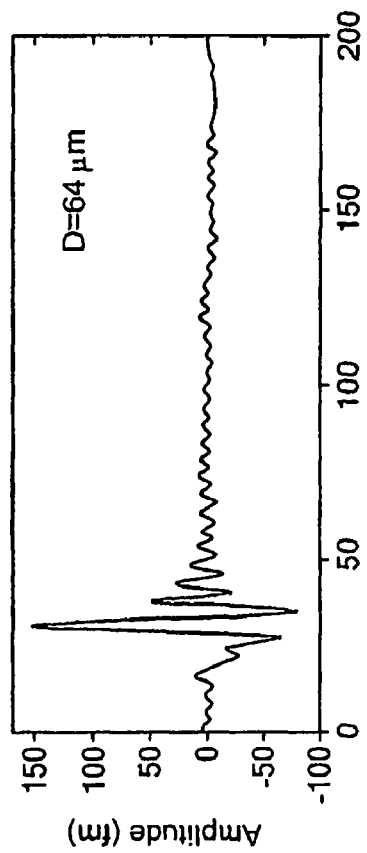
Figure 9B:
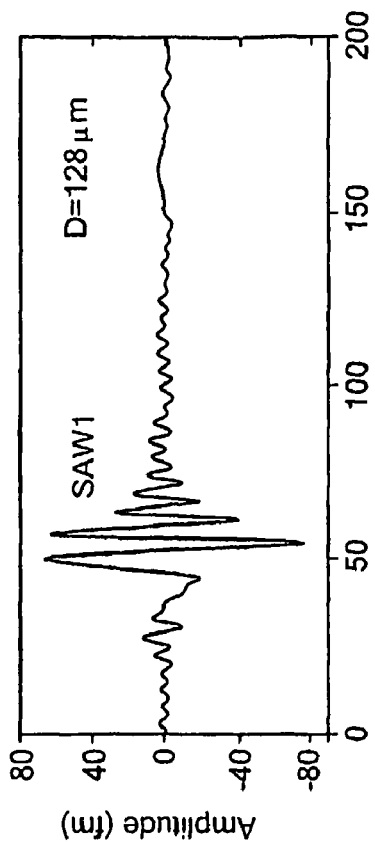
Figure 9C:
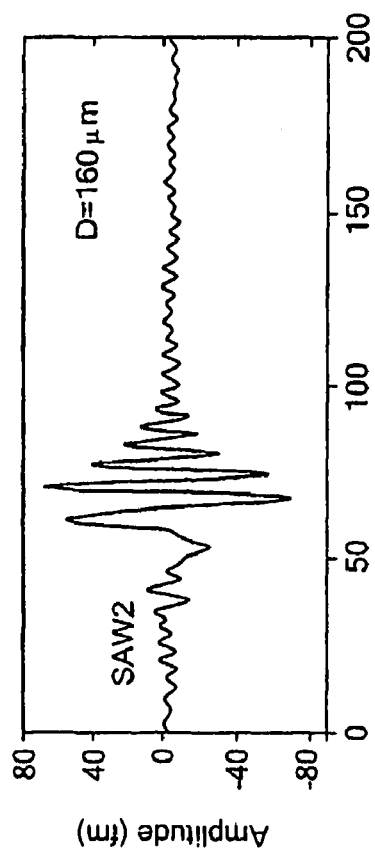
Figure 9D:
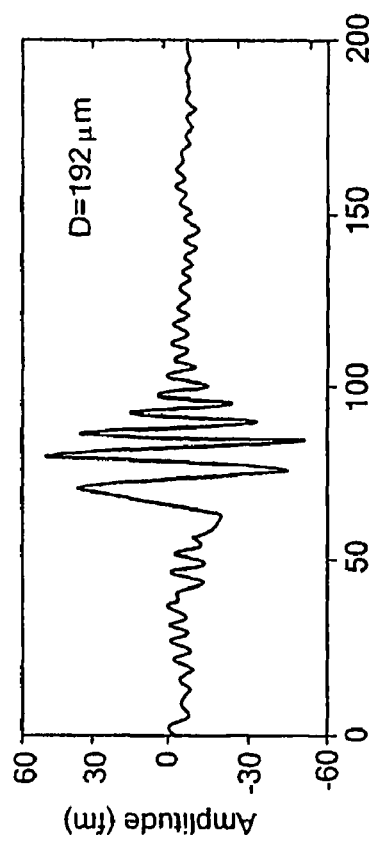

FIGS. 8a and 8b represent similar processing conducted on a semi-infinite substrate 94 of FIG. 8c at different test beam application points D. This figure illustrates one of the advantages of converting the signal from the frequency domain back to the time domain. The small arrival labeled "Edge reflection of SAW 83" is a due to the presence of a defect in the material surface. In the frequency domain data, this defect is not clearly evident as the frequency components of this signal overlap the frequency components of the larger, direct SAW arrival. Time domain reconstruction can be very useful in detecting signals scattered from defects or interfaces. Upon conversion to the time domain, these signals can be time gated and subsequently analyzed. These signals were obtained by inverse Fourier transforming the frequency domain data measured at a bandwidth of 0.7 Hz at each point in processor 71.

FIGS. 9a-9f illustrate the application of a surface acoustic wave producing laser beam on a 240 nanometer thick gold film 98 on a fused silica substrate 100. The wave forms are reconstructed from frequency domain data taken over the range of 100 KHz to 200 MHz. The bandwidth of the optical detection system at each frequency was 0.7 Hz at each measurement point. The dispersion in the waveforms is clearly seen; as the source to receiver distances D are increased, the waveforms are seem to spread out in time. Conventional processing of the time domain data allows for the dispersion curve to be obtained. In addition, comparison with theoretical dispersion curves, through application of an inversion algorithm, e.g., an optimizations routine is then used to determine the mechanical or physical properties (thickness, for example) of the film.

Figure 10A:
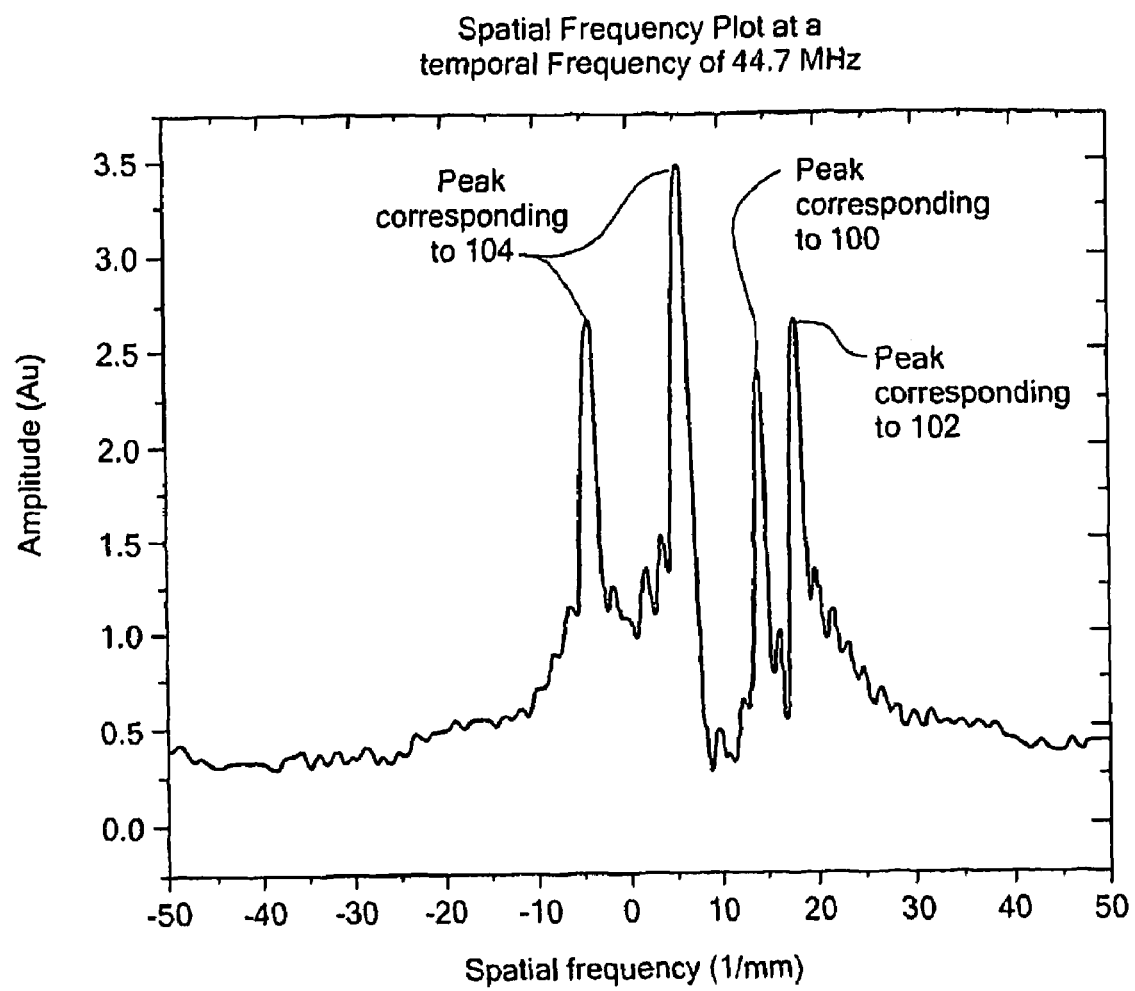
FIGS. 10a and 10b illustrate the processing of data in a thin plate to obtain the dispersion (velocity at each frequency) curve.
Figure 10B:
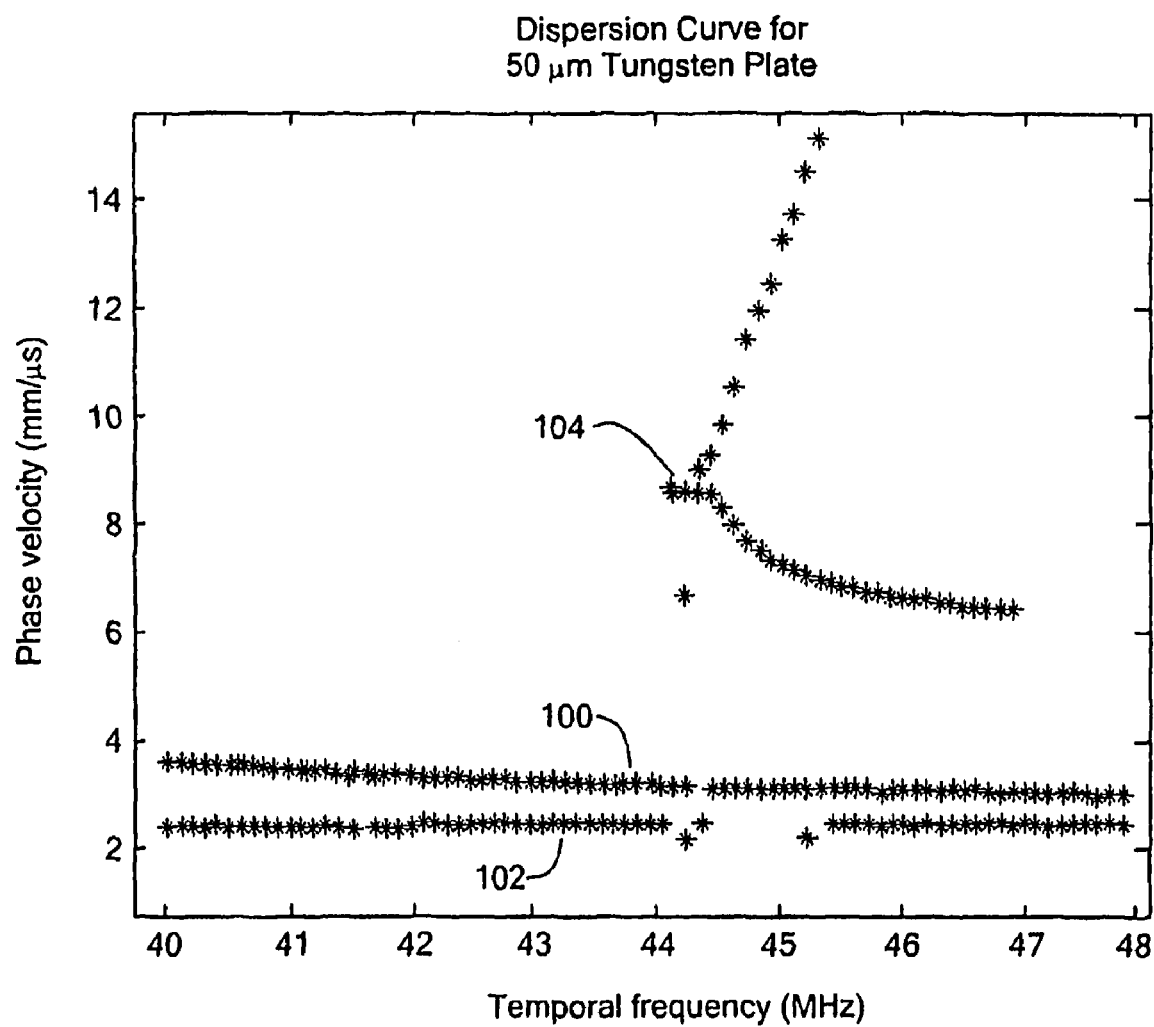

FIG. 10 illustrates an example of obtaining a dispersion curve through the method outlines in FIG. 3. The sample was a 50 micron tungsten plate. Measurements were taken at 60 spatial points in source to receiver distance increments of 10 microns. At each measurement temporal frequency, a Fourier transform was performed on the experimental data obtained from all of the spatial positions. An example of the result of this is shown in FIG. 10a, for a temporal frequency of 44.7 MHz. Peaks in the spatial frequency curves then correspond to acoustic modes in the system. In a free-standing thin plate, acoustic plate waves or Lamb modes are generated, and at each temporal frequency, more than one mode is excited. These are labeled in FIG. 10b as 100, 102, and 104 and these correspond to the first antisymmetric plate mode, the first symmetric plate mode, and the second antisymmetric plate mode. These modes have different acoustic wave velocities and thus can be effectively separated in the spatial frequency domain as shown in FIG. 10a. The corresponding dispersion curve shown in FIG. 10b can be used to find the thickness or mechanical properties of the plate through comparison with theoretical dispersion curves using a standard optimization routine.

What is claimed is:

1. Apparatus for analyzing thin surface layers comprising:
   A source of laser radiation;
   Means for modulating the laser radiation at a single frequency, capable of operating over a broad bandwidth from the MHz-GHz frequency range;
   An optical system for directing the modulated radiation to at least a first point on a surface of a thin surface layer to cause an acoustic wave therein;
   Means for sensing a response of the thin surface layer to the acoustic wave;
   Means for limiting the sensor bandwidth to a narrow frequency range; and
   Means for analyzing the sensed response to provide an indication of properties of the thin surface layer.

2. The apparatus of claim 1 wherein said laser source is operating at or around 1.5 micron.

3. The apparatus of claim 1 wherein said laser source is operating at or around 1.3 microns.

4. The apparatus of claim 1 wherein said laser source is operating at or around 1.064 microns.

5. The apparatus of claim 1 wherein said laser source includes an electro-absorption modulator to modulate the amplitude of the laser.

6. The apparatus of claim 1 wherein said laser source includes a Mach Zehnder modulator to modulate the amplitude of the incident laser radiation.

7. The apparatus of claim 1 wherein said laser source includes an electro-optic modulator to modulate the amplitude of the incident laser radiation.

8. The apparatus of claim 1 wherein said laser radiation source includes an erbium fiber amplifier to amplify the laser radiation.

9. The apparatus of claim 1 wherein said optical system includes lens for focusing the laser radiation to a spot on said thin surface layer.

10. The apparatus of claim 8 further including means for adjusting the position for said laser radiation relative to said thin surface layer.

11. The apparatus of claim 1 wherein said sensing means further includes:

a second source of detection laser radiation;

a second optical system for applying said detection radiation to said thin surface layer at a second point and receiving return radiation therefrom; and means for analyzing the returned radiation for information on the condition of said thin surface layer.

12. The apparatus of claim 11 wherein said second optical system includes an optical interferometer for detecting the displacement or velocity of the sample surface.

13. The apparatus of claim 11 wherein said sensing means includes means for detecting over a frequency range at a fixed distance between the first and second points and means for Fourier transforming to convert the signals from a frequency domain into a time domain for analysis.

14. The apparatus of claim 1 further including a RF lock-in amplifier or a network analyzer providing narrow bandwidth detection of the acoustic waves.

15. The apparatus of claim 13 including means for moving said first point in evenly spaced steps, and means for detecting real and imaginary components at each step using a Fourier transform to determine spatial frequencies of acoustic modes and acoustic wave velocities by dividing a detected temporal frequency by spatial frequencies of the acoustic modes.

16. The apparatus of claim 1 wherein said thin surface layer is selected from the group consisting of thin films, coatings, MEMS devices, NEMs devices, liquid based bio-samples.

17. A method of analyzing properties of thin surface layers using the apparatus of claim 1.

18. The apparatus of claim 9 further including means for adjusting the position for said laser radiation relative to said thin surface layer.

19. The apparatus of claim 12 wherein said sensing means includes means for detecting over a frequency range at a fixed distance between the first and second points and means for Fourier transforming to convert the signals from a frequency domain into a time domain for analysis.

20. The apparatus of claim 19 including means for moving said first point in evenly spaced steps, and means for detecting real and imaginary components at each step using a Fourier transform to determine spatial frequencies of acoustic modes and acoustic wave velocities by dividing a detected temporal frequency by spatial frequencies of the acoustic modes.

* * * * *

UNITED STATES PATENT AND TRADEMARK OFFICE
CERTIFICATE OF CORRECTION

| | | |
|---|---|---|
| PATENT NO. | : 7,649,632 B2 | |
| APPLICATION NO. | : 10/593655 | |
| DATED | : January 19, 2010 | |
| INVENTOR(S) | : Todd W. Murray | |

It is certified that error appears in the above-identified patent and that said Letters Patent is hereby corrected as shown below:

Title page, Item (75) Inventor: "Brookline" should read --Roslindale--.

Signed and Sealed this
Twelfth Day of April, 2011

David J. Kappos
*Director of the United States Patent and Trademark Office*